United States Patent [19]

Clément

[11] 4,042,335

[45] Aug. 16, 1977

[54] INTEGRAL ELEMENT FOR ANALYSIS OF LIQUIDS

[75] Inventor: Pierre L. Clément, Paris, France

[73] Assignee: Eastman Kodak Company, Rochester, N.Y.

[21] Appl. No.: 691,265

[22] Filed: June 25, 1976

Related U.S. Application Data

[63] Continuation-in-part of Ser. No. 598,462, July 23, 1975, abandoned.

[51] Int. Cl.² ............................................. G01N 31/22
[52] U.S. Cl. .......................... 23/253 TP; 195/103.5 R
[58] Field of Search ............ 23/253 TP; 195/103.5 R; 426/87, 88; 116/114 AM, 114 P

[56] References Cited

U.S. PATENT DOCUMENTS

| | | | |
|---|---|---|---|
| 3,092,465 | 6/1963 | Adams, Jr. et al. | 23/253 TP |
| 3,243,303 | 3/1966 | Johnson | 426/88 |
| 3,526,480 | 9/1970 | Findl et al. | 23/253 R |
| 3,672,845 | 6/1972 | Verbeck | 23/253 TD |
| 3,723,064 | 3/1973 | Liotta | 23/253 TP |
| 3,791,933 | 2/1974 | Moyer et al. | 23/253 TP X |
| 3,847,553 | 11/1974 | Verbeck | 23/253 TP |
| 3,897,214 | 7/1975 | Lange et al. | 23/253 TP |
| 3,901,657 | 8/1975 | Lightfoot | 23/253 TP |

*Primary Examiner*—Robert M. Reese
*Attorney, Agent, or Firm*—R. P. Hilst

[57] ABSTRACT

The present invention concerns a multilayer element for the analysis of liquids such as biochemical and biological liquids. Elements according to the invention include (1) a reagent layer including a composition that is interactive in the presence of a predetermined substance to be analyzed (analyte) to provide a diffusible, detectable species, and (2) a registration layer that is permeable to the detectable species and within which such species, e.g., a dye, can be detected. Also within the element, preferably between the reagent layer and the registration layer, there can be a radiation-blocking layer, such as an opaque reflecting layer, to enhance detection of the diffusible species within the registration layer. The element can also include a spreading layer, preferably separated from the registration layer by a reagent layer. In operation, a sample of liquid under analysis is applied to the reagent layer of the element or, if present, to a spreading layer. If the sample contains analyte that the element is intended to detect, chemical reaction or other interaction within the reagent layer provides a detectable species that diffuses, via any intervening layers such as a radiation-blocking layer, into the registration layer for detection there, such as by radiometric techniques like reflection spectrophotometry.

20 Claims, 4 Drawing Figures

INTEGRAL ELEMENT FOR ANALYSIS OF LIQUIDS

This is a continuation-in-part of U.S. Pat. Application Ser. No. 598,462, filed July 23, 1975 and now abandoned.

BACKGROUND OF THE INVENTION

1. Field of the Invention

Chemical analysis of liquids such as water, foodstuffs like milk, and biological liquids is often desirable or necessary. Various elements to facilitate liquid analyses are known. Such elements have often included a reagent for a substance under analysis, termed analyte herein, which reagent, upon contacting a liquid sample containing the analyte, effects formation of a colored material or another detectable change in response to the presence of the analyte. Such elements include, for example, pH test strips and similar indicators wherein a paper or other highly absorbent carrier is impregnated with a material, chemically reactive or otherwise, that responds to contact with liquid containing hydrogen ion or other analyte and either generates color or changes color. Depending on the selection of responsive material, the change is usually qualitative or, at best, semiquantitative. In certain fields, it is often required that analytical techniques yield rapid, quantitative results. Much recent development work has attempted to provide elements useful in diagnostic chemical analysis, where testing of biological liquids including body fluids such as blood, serum, urine and the like must produce highly quantitative results, rapidly and conveniently.

Solution chemical techniques have enjoyed broad acceptance in the clinical laboratory environment, particularly in automated analysis. Such techniques, however, require analyzer equipment having intricate solution handling and transport capabilities. Analytical equipment of the "wet chemistry" variety, illustrated for example in U.S. Pat. No. 2,797,149, is often expensive and may require skilled personnel, both for operation and to maintain the high level of cleanliness that is needed to avoid sample to sample contamination.

As an alternative to solution chemistry, various multilayer integral elements for non-solution, essentially dry chemical analysis have been proposed. The term "integral", as used herein to describe analytical elements, refers to elements containing two or more desirably discrete layers that under conditions of use are superposed and in substantially continuous intimate contact with adjacent layers in the element. Although essentially dry analysis offers substantial storage, handling and other conveniences as compared to wet chemistry, variations of the "dry" approach have enjoyed only limited success and have been used primarily for qualitative and semi-quantitative test purposes.

2. Description of Related Art

A basic variety of integral analytical element is described in U.S. Pat. No. 3,092,465. Such multi-layer elements use an absorbent fibrous carrier impregnated with one or more reagents, typically including a color former, over which is coated a semi-permeable membrane. Upon contact with a test liquid, analyte passes through the membrane and into the fibrous carrier to generate color in an amount related to the concentration of analyte. The membrane prevents passage and absorption of certain interfering components, such as red blood cells, that could impair accurate reading of the color provided as a test result.

Analytical elements that rely on absorbent filter papers or other fibrous media to receive and distribute a liquid sample have not been popular, compared to wet chemical procedures, in applications such as clinical laboratory testing, presumably due to their inability to produce high accurate, quantitative results. It is described in the literature that diagnostic elements using impregnated bibulous materials, such as fibrous filter papers, can produce non-uniform test results. In U.S. Pat. No. 3,050,373, it is mentioned that precipitation can occur in the impregnating solutions, thereby impairing uniform distribution of reagent within the bibulous carrier or matrix. Also, elements using fibrous, bibulous materials are susceptible to the occurrence of a non-uniformity in test result that is termed "banding." "Banding" is exemplified by a test result occurring to a greater extent in one portion of the region of the element experiencing a test result, such as at the periphery of the region penetrated by an applied sample. It is apparently the result of extensive and extremely non-uniform migration of sample components or reagent chemicals within the bibulous material, possibly due to chromatographing, to provide high local concentrations of such chemicals. Gelatin and gelatin-like materials are described in U.S. Pat. Nos. 3,061,523 and 3,104,209 as useful constituents of the impregnating solution, due apparently to their ability to restrain the high rate of such migration and consequently to encourage improvements in test result uniformity. However, gelatin and gelatin-like materials in the fibrous, reagent containing bibulous matrix decrease the rate of sample uptake as compared to the more highly absorbent gelatin-free matrix. Such decreased absorption can leave surface liquid on the element and necessitate washing the element to remove the excess prior to making a test determination. As a result, an upper limit on the amount of gelatin to be impregnated into a bibulous matrix is typically specified. Such properties also characterize analytical elements using, without more, layers solely of gelatin or similar materials, as discussed in U.S. Pat. No. 3,526,480.

Integral analytical elements adapted for automated test procedures have also been described, such as in U.S. Pat. Nos. 3,368,872 and 3,526,480. Such descriptions refer to means for avoiding chromatographic effects (often called ringing, targeting, doughnuting or banding) in the element by immobilizing reagent or including a means to decrease the tendency of an applied sample to exert a washing effect on incorporated reagent, as by use of simple porous members over an absorbent, reagent containing material, such as fibrous filter paper. However, there is no suggestion in such descriptions of using within an element a means that not only takes up a liquid sample but also provides a uniform apparent concentration of a sample component such as analyte to substantially the entire portion of a reagent layer surface that is contacted by an applied sample. Such uniform apparency of concentration is extremely important in obtaining test results appropriate for interpretation by automated readout, whether densitometric, colorimetric, fluorimetric, or otherwise. This is true even in the absence of gross non-uniformities such as those introduced by chromatrographic effects.

A means to provide somewhat uniform concentration of analyte to the reagent areas of an element for dry analysis has been by a technique that can be termed sample confinement. Usually, as is described in U.S. Pat. No. 3,368,872, a barrier is included on the element to confine an applied sample in a predetermined region of the element's surface, with the result that excess liquid is usually present on the element after sample application. This can create inconveniences, as in the handling and cleanup of excess sample remaining on the element and, more seriously, can require extremely precise sample volume delivery when applying sample to the element.

There has been some recognition of the need to promote or avoid, as described, the migration of material between layers of integral analytical elements, as is discussed in U.S. Pat. Nos. 2,761,813; 2,672,431; 3,672,432; 2,677,647; 2,923,669; 3,814,670 and 3,843,452. However, this has been in the context of elements for determining the presence of micro-organisms, and the elements described for such purposes typically include at least one layer comprising a fibrous matrix and require non-discrete layers, the interface of which is a blend of the adjacent layers.

Until very recently, there was no suggestion in art relating to analytical elements of a layer or other means to receive sample constituents and to encourage them to distribute within that layer to achieve therein an apparent concentrational uniformity of analyte, analyte products or other substances to be provided, in such uniform apparent concentration, to an associated layer for analytical reactions or similar activity. In fact, as was apparently well recognized, the structural and chemical characteristics of bibulous and other fibrous materials used in most known analytical elements (such as absorbent cellulosic filter papers, glass fiber papers, wood, etc.) might impair such a result for reasons of physical restraint, non-uniform permeation of sample constituents or undesirable chemical binding. Additionally, the choice of fibrous materials can frustrate highly accurate measurement due to severe non-uniformity in properties such as structure and texture. It is known, for example, that in the preparation of papers, starting fibers are often processed to form smaller constituent fibers, called tendrils, that increase the strength of the resultant paper. The term "fibrous," as used herein to describe materials such as papers and the like, refers to materials prepared using preformed fibers or strands that are present in the finished material. Exemplary fibers used in preparing fibrous materials are described in U.S. Pat. No. 3,867,258.

Non-uniformity in the detectable color response or other test result obtained when using integral analytical elements incorporating fibrous materials has been recognized as a problem associated with the use of such elements. Improved devices using such materials to provide absorbent layers have sought to overcome the gross effect of such non-uniformity, but they have not succeeded in avoiding the problem. As an example, U.S. Pat. No. 3,723,064 describes an analytical element that includes regions of different effective permeability to an analyte or reaction product of an analyte and produces a plurality of spaced-apart, threshold color indications as an analytical result. Although the desirability of a smoothly continuous response in manifest, an element made as described in the U.S. Pat. No. 3,723,064 patent can only yield an approximate analytical result, the accuracy of which varies indirectly with increased spacing between thresholds. If the difference in permeability between regions were decreased, to narrow the interval between thresholds in the interest of increased response precision over the intended dynamic range, the complexity of elements made in accordance with the U.S. Pat. No. 3,723,064 patent would increase dramatically. No suggestion is made as to how one might improve the uniformity and precision of a continuously varying test result and, however optimized, elements of the U.S. Pat. No. 3,723,064 patent would produce a discontinuous response that would apparently be non-uniform within each region of permeability due to non-uniformities associated with the use of filter papers and other fibrous materials present in that element.

U.S. Pat. No. 3,791,933 describes a multi-component device for the assay of enzyme substrates and metabolites, such as in body fluids. It describes a clamped array adapted to receive a test sample, filter out or otherwise remove large sample constituents (such as proteins) and effect a test reaction to produce a detectable result, such as the generation of a color. Although glass fiber paper is disclosed as assisting in distributing a reaction mixture across a plastic viewing window, such material apparently merely assists the outward diffusion of liquid sample within the glass fiber layer to enlarge the region of the element exhibiting a test result and thereby render the result more easily visible. There is no suggestion of any means to form within the region of diffusion a concentrational uniformity of analyte, which, of course, is extremely important for the production of an analytical result that is of a uniform nature and, as such, precisely detectable. Further, the glass fiber is apparently observable to a means of detection.

Improved multilayer integral analytical elements are described in French Patent Application 7,323,599, filed June 28, 1973, now French Pat. No. 2,191,734, and in U.S. Patent Application Ser. No. 538,072, filed Jan. 2, 1975 now U.S. Pat. No. 3,992,158. Such elements can receive a liquid sample and spread the sample within a spreading layer of the element to obtain in the element a uniform apparent concentration of analyte, other appropriate sample constituent or analyte product and produce in the presence of analyte an analytical result that, by virtue of its uniformity, can be measured quantitatively by automated devices, using techniques such as spectrophotometry, fluorimetry, etc. Elements disclosed in French Pat. No. 2,191,734, include spreading layers and reagent layers that contain a reactive or otherwise interactive material that, by virtue of its activity, promotes in the element a radiometrically detectable change, such as a color change.

In providing an analytical result, whether in a bibulous test strip, other predominantly fibrous element or in an element of the type described in French Pat. No. 2,191,734 and in the above-mentioned U.S. Application Ser. No. 538,072, difficulties in obtaining or measuring a detectable change within the element may be experienced. For example, the fluid under analysis or by-products of the analytical reaction can provide, within the reagent mixture, constituents that interfere with detection of the test result. Also, popular reagent matrix materials such as filter papers can be opaque, allowing detection of an analytical result only at the surface of the matrix material and not throughout its thickness. This can diminish the observable magnitude and range of an analytical result, resulting in an inability to measure effectively both low concentrations of analyte and subtle changes in analyte concentration. It is considered desirable, therefore, to have elements for analysis of liquids in which the materials characterizing the test result can be detected without hindrance from chemical or optical interferants, opaque matrix materials, or the like.

Accordingly, although various test strips and improved analytical elements, e.g., those of French Pat. No. 2,191,734 can be desirable for qualitative and quantitative dry analysis of liquids, comparable, more interference-free elements would be desirable.

SUMMARY OF THE INVENTION

The present invention provides novel integral elements for analysis of liquids, such as biological liquids. As referred to herein, the terms "integral element" and "integral analytical element" refer to composite elements including an array of at least two superposed layers that in fluid contact under conditions of use. Elements of this invention are capable of performing internally a variety of sample handling and/or processing functions. They do not require expertise in their use and, especially in their preferred embodiments, they can produce quantitative analytical results witout specialized spotting or other procedures such as sample confinement, washing or other removal of excess sample. Further, results that can be produced by elements of this invention intended for quantitative analysis are substantially consistent and free from deleterious internal variations so that automated means of measuring electromagnetic radiation (radiometric techniques) can be used to detect such results, if necessary or desirable, with minimal risk of inconsistency.

Stated more particularly, the present invention provides integral analytical elements composed of multiple, superposed layers which can provide quickly within the element a detectable change in response to the presence of a predetermined analyte in liquid applied to the element. Elements of this invention can be used for diagnostic analysis of biological liquids, such as blood, blood serum or urine, and include, (1) a reagent layer that is permeable to at least analyte or an analyte precursor and which has therein a composition containing material that is interactive in the presence of analyte to provide a detectable chemical species, such as a dye, that is diffusible within the element and (2) a registration layer that is permeable to the detectable species and within which the detectable species can be detected, such as by radiometric techniques.

The reagent layer can use a fibrous reagent matrix such as filter paper, woven fabric, fibrous fleece or matting. This is common when qualitative or semi-quantitative results are desired. In various preferred embodiments, non-fibrous reagent layers are preferred and are considered optimal for quantitative measurements. Such layers usually use a hydrophilic colloid reagent matrix, as will be explained in greater detail below. Registration layers as described herein are generally prepared without the inclusion of any chemically reactive materials or other materials that would interfere with appropriate result detection in a particular analysis. The various layers of the present elements can be carried on a radiation-transmissive support. As used herein, the term "radiation-transmissive" describes supports and other layers of an analytical element that permit effective passage of electromagnetic radiation used to detect an analytical result produced in the element. Such transmissiveness includes transmission of electromagnetic radiation of a wavelength or wavelengths within the region between about 200 nm and 900 nm, and also of detectable radiation as is produced by radioactivity. Radiation-transmissive layers and supports can be transparent, if desired, and this may be beneficial, especially for measurements to be made at low levels of radiation. When the element includes a support, the registration layer is interposed between the support and the reagent layer and usually is adjacent to the support.

The elements of this invention can include a radiation-blocking layer, which is usually interposed between the reagent layer and the registration layer. The radiation-blocking layer is a layer that contains one or more opacifying agents and inhibits passage in or through such layer of electromagetic radiation, such as at the wavelength or wavelengths used for excitation and/or detection of a species within the registration layer.

In certain preferred embodiments, the subject elements can include a sample spreading layer that, at least under conditions of use, is in fluid contact with other layers of the element, such as the reagent layer and the registration layer. The sample spreading layer, synonymously referred to herein as a spreading layer or a metering layer, is capable of distributing or metering within the layer substance(s) including an analyte or an analyte precursor in a liquid sample applied to the element to provide, at any given time, a uniform apparent concentration of such substance at the surface of the spreading layer facing, i.e., closer to, the reagent layer. The applied sample need not be confined to obtain such uniform concentration which, although it will be uniform at any point of time can change over a period of time without deleterious effects. The spreading layer is isotropically porous; that is, it is porous in every direction within the layer. Reference herein to isotropic porosity identified the fact of porosity in all direction within the spreading layer. It will be understood that the degree of such porosity may be variable, if necessary or desirable, for example, regarding pore size, percentage of void volume or otherwise. The term isotropic porosity (or isotropically porous) as used herein should not be confused with the terms isoporous or ionotropic, often used with reference to filter membranes to signify those membrances having pores that are continuous between membrane surfaces. Likewise, isotropic porosity should not be confused with the term isotropic, used in contradistinction to the term anisotropic, which signifies filter membranes having a thin "skin" along at least one surface of the membrane. See for example, *Membrane Science and Technology*, James Flinned, Plenum Press, New York (1970).

For quantitative analytical procedures, the reagent layer is preferably of substantially uniform permeability to at least one substance spreadable within the spreading layer and to the diffusible detectable species provided in the reagent layer by virtue of the interaction described herein. In such cases the registration layer is preferably of substantially uniform permeability to the detectable species.

Uniform permeability of a layer refers to permeability such that, when a homogeneous liquid is provided unifomly to a surface of the layer, identical measurements of the concentration of such fluid within the layer, but made through different regions of a surface of the layer, will usually yield substantially equal results. By virtue of uniform permeability, undesirable concentration gradients can be avoided within, for example, a reagent layer. It is not necessary that all possible measurement techniques produce such results. The desirability of a particular technique and of specific measurement parameters will depend on the physical characteristics of the layer, such as its tendency to transmit, absorb, or scatter radiation. The selection in any instance of an appropriate measurement technique (e.g., colorimetric, densitometric, fluorimetric) and of appropriate measurement parameters (e.g., aperture size and configuration) will be apparent to those familiar with analytical procedures.

As discussed elsewhere herein, uniform permeability is not considered characteristic of fibrous materials such as filter paper. It is believed that factors such as variable wicking action within a fibrous material, differences in fiber size or spacing and the like, can effect the formation within such fibrous materials, and also in associated materials in fluid contact therewith, of variations in the apparent concentration of permeant liquids. This of course, introduces undesirable bias between test measurements made within regions having different apparent concentrations. Uniform permeability of reagent, registration or other layers, within an analytical element is desirable as a means of facilitating the production of quantitative analytical results. The analytical significance of results produced in elements not having uniformly permeable layers can be limited. Also, the efficiency of result detection in such elements may be impaired, for example if irregularly occurring concentrational or other discontinuities, seen by a means of detection, are present within an element.

Reference herein to fluid contact between a spreading layer, a reagent layer and/or other layers of an integral analytical element as described herein identifies the ability of a fluid, whether liquid or gaseous, to pass in such element between superposed regions of such layers. Stated in another manner, fluid contact refers to the ability of components of a fluid to pass between the layers in fluid contact. In the case of analysis for nitrogen containing compounds, ammonia or other nitrogen containing gaseous materials may comprise fluid passing between such layers. Although layers in fluid contact can be contiguous, they may also be separated by intervening layers. However, layers in the element that physically intervene layers in mutual fluid contact will also be in fluid contact therewith and will not prevent the passage of fluid between such layers.

Fluid contact between layers can be achieved by preparing elements having layers that are initially contiguous or effectively so for purposes of fluid passage. Alternatively, it may be appropriate to prepare elements that have layers initially non-contiguous, and which further can be spaced apart, such as by the use of interleaves as described, for example, in U.S. Pat. No. 3,511,608 or by the use of a resilient absorbent material or deformable supports as described in U.S. Pat. No. 3,917,453 and 3,933,594. As will be appreciated, if the element has initially non-contiguous layers, it may be necessary to apply compressive force or otherwise provide means to bring layers of the element into fluid contact at the time of its use to provide an analytical result.

As used in the specification and claims herein, the term "diffusible" denotes the capability of a material to move effectively within an analytical element by diffusion when that material is carried in liquid present in the element, such as the solvent or dispersion medium of a liquid sample applied to the element. Similarly, the term "permeable" denotes the ability of a substance or layer to be penetrated effectively by a material carried, i.e., distributed in as by dissolution or dispersion, in a liquid.

In operation, an exemplary analytical element of this invention can receive a liquid sample which, if analyte positive, initiates a chemical reaction or other interaction within the reagent layer to provide a diffusible, preferably radiometrically detectable species that diffuses from the reagent layer into the registration layer where it can be detected. If necessary or desirable, a radiation-blocking layer can be provided in the element between the reagent layer and the registration layer, for example to screen out red blood cells, if analyzing whole blood, or to isolate other materials from being observed during detection of an analytical result in the registration layer. If a metering layer is included in an element, an applied sample will usually pass through the metering layer prior to entering the reagent layer, an analyte or an analyte precursor will be distributed within the metering layer to provide a uniform apparent concentration of such material at the surface of the metering layer facing the reagent layer. It is possible to obtain such uniform apparent concentration over a wide range of sample volumes applied to the element. Due to fluid contact between the metering layer and the reagent layer and also to the preferred uniform permeability of the reagent layer to substance spread within the spreading layer or to products derived from such substance, uniformly metered constituents are provided from the spreading layer to the reagent layer and can penetrate the reagent layer essentially without the occurrence therein, at any instant in time, of significant variations in the apparent concentration of such substance or products thereof. Due to the presence of an interactive (e.g., chemically reactive) material, and a uniform apparent concentration of substance provided from the metering layer to the reagent layer, a uniform quantitative detectable change can be produced in the element. Such a change, which can be the generation or destruction of coloration or fluorescence, can be detected quantitatively by radiometric techniques and, if desired, by automatic radiometric sensing devices such as photometric or fluorimetric devices.

BRIEF DESCRIPTION OF THE DRAWINGS

In the accompanying drawings, each of FIG. 1, FIG. 2, FIG. 3

DESCRIPTION OF PREFERRED EMBODIMENTS

Figure 1:
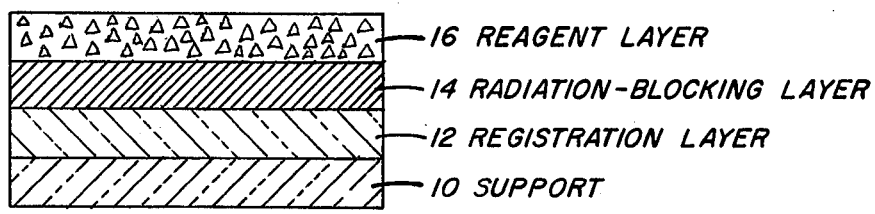

The integral elements of this invention include a reagent layer and a registration layer that is preferably radiation-transmissive. Such elements can have the layers on a support, preferably radiation-transmissive, or if the layers demonstrate appropriate durability and integrity, a support is not needed.

In one preferred embodiment, an integral analytical element of this invention comprises a radiation-transmissive support having thereon, (1) a reagent layer that is permeable to at least analyte or an analyte precursor and which contains a composition that is interactive in the presence of analyte to provide a diffusible, detectable species, (2) a radiation-blocking layer that is permeable to the detectable species, and (3) a radiation-transmissive registration layer that is permeable to the detectable species and within which the detectable species can be detected. Optionally, the registration layer can include a mordant for the detectable species. The registration layer is preferably interposed between the support and the radiation-blocking layer, with the radiation-blocking layer interposed between the registration layer and the reagent layer. Also, the reagent layer is preferably of substantially uniform permeability to analyte (also to be an analyte precursor if appropriate) and to the diffusible, detectable species. The registration layer is of such permeability as regards the detectable species. The radiation-blocking layer, although usually not considered disruptive of the apparent concentration of detectable species provided to the radiation-blocking layer from the reagent layer, is desirably of uniform permeability to the detectable species. Preferred radiation-blocking layers include an opacifying agent such as a pigment, a polymer in appropriate form such as a blushed polymer, or both. In one aspect of this embodiment the radiaton-blocking layer and registration layer are non-fibrous.

In accordance with another preferred embodiment of the present invention, there is provided an integral analytical element with a support having thereon a reagent layer, a registration layer and, optionally, a radiation-blocking layer, all as described above with respect to the foregoing preferred embodiment. Additionally, however, there is included in elements according to this preferred embodiment a non-fibrous spreading layer, desirably isotropicaly porous and positioned on the element such that the reagent layer is interposed between the registration layer and the spreading layer. In one aspect of this embodiment, all layers are preferably non-fibrous, to enhance quantitative analytical capability of the element. The term "non-fibrous" is used herein with respect to layers and/or materials to indicate that such layers or materials are free or substantially free from fibrous materials, that is, they do not include fibrous components to a degree that would interfere with sample spreading as discussed herein or with detection of the anayltical result by radiometric means.

When used in association with a spreading layer, reagent layers in the elements of this invention are desirably unfirmly permeable, and optionally porous if appropriate, to substance spreadable within the metering or spreading layer and to reaction products thereof or products formed as a result of the interaction of such substance. As used herein the term permeability includes permeability arising from porosity, ability to swell or any other characteristic. Reagent layers can include a matrix in which the interactive material is distributed, i.e., dissolved or dispersed. The choice of a matrix material is, of course, variable and dependent on the intended use of the element. Desirable matrix materials for reagent layers associated with spreading layers are non-fibrous and can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol)and poly(vinyl pyrrolidone), acrylamide polymers, etc. Organophilic materials such as cellulose esters and the like can also be useful, and the choice of materials in any instance will reflect the use for which a particular element is intended. To enhance permeability of the reagent layer, if not porous, it is often useful to use a matrix material that is swellable in the solvent or dispersion medium of liquid under analysis. Also, it may be necessary to select material that is compatible with the application of an adjacent layer, such as by coating means, during manufacture of the element. As an example, where the formation of discrete, contiguous layers is desired and the intended analysis will be of aqueous liquids, it may be appropriate to select an essentially water soluble matrix for the reagent layer and essentially organosoluble or organo dispersible ingredients for an adjacent layer, such as a spreading layer. In such manner, mutual solvent action is minimized and a clearly delineated layer structure can be formed. In many cases, to facilitate the formation within the spreading layer of such apparent concentrational uniformity as is discussed herein, it may be desirable to have the reagent layer of lower permeability than is the spreading layer itself. Relative permeability can be determined by well-known techniques.

Within the reagent layer is distributed a composition, including on or more active materials, that is interactive in the presence of a predetermined analyte. Optionally, the interactive composition can also interact with, or otherwise in the presence of, a precursor or reaction product of such an analyte, if appropriate in view of the analysis of choice, such as in elements intended to determine cholesterol, which in serum is present in esterified form, and triglycerides, which are often analyzed on the basis of the glycerol component of triglycerides. The term "interactive" is meant herein to refer to chemical reactivity, catalytic activity as in the formation of an enzyme-substrate complex, or any other form of chemical or physical interaction able to produce or promote within the element, such as in the reagent layer, the formation of a diffusible species that is detectable, for example, by suitable measurement of light or other electromagnetic radiation. The distribution of interactive composition can be obtained by dissolving or dispersing it in a matrix material, if used. Although uniform distributions are often preferred, they may not be necessary if an interactive material in turn the composition is, for example, an enzyme. Reagents or other interactive materials soluble in the liquid under analysis may advantageously be immobilized in the reagent layer, particularly when the reagent layer is porous. The particular interactive materials that may be distributed within a reagent layer will depend on the analysis of choice. In the case of many analyses, enzymes such as oxidase materials like glucose oxidase or cholesterol oxidase may desirably be included as interactive materials within a reagent layer of an element intended for the analysis of analyte that is a substrate for such enzyme. As an example, an oxidative enzyme can be incorporated into a reagent layer together with peroxidase or a peroxidative material and a material or composition that, upon oxidation in the presence of peroxidase (or another substance having peroxidative activity) and the hydrogen peroxide formed upon interaction of an oxidase and its substrate, provides a dye or other detectable species. In the practice of this invention, the detectable species is diffusible such that it can move into the permeable registration layer. Such diffusivity can be imparted to detectable species not inherently diffusible by means known to those skilled in chemical synthesis, usually by the addition of chemical groups that impart the desired solubility. Where aqueous liquids are to be analyzed, solubilizing groups such as hydroxyl groups, carboxyl groups, sulfonic acid groups and the like can be useful for purposes of solubilization.

Materials or compositions that contain an oxidizable material and can provide a detectable species include certain dye-providing compositions. In one aspect, dye-providing compositions can include a compound that, when oxidized, can couple with itself or with its reduced form to provide a dye. Such autocoupling compounds include a variety of hydroxylated compounds such as orthoaminophenols, 4-alkoxynaphthols, 4-amino-5-pyrazolones, cresols, pyrogallol, guaiacol, orcinol, catechol phloroglucinol, p,p-dihydroxydiphenyl, gallic acid, pyrocatechoic acid, salicyclic acid, etc.. Compounds of this type are well known and described in the literature, such as in *The Theory of the Photographic Process*, Mees and James Ed, (1966), especially at Chapter 17. In another aspect, the detectable species can be provided by oxidation of a leuco dye to provide the corresponding dyestuff form. Representative leuco dyes include such compounds as leucomalachite green and leucophenolphthalein. Other leuco dyes, termed oxichromic compounds, are described in U.S. Pat. No. 3,880,658 and it is further described that such compounds can be diffusible with appropriate substituent groups thereon. The non-stabilized oxichromic compounds described in U.S. Pat. No. 3,880,658 are considered preferable in the practice of this invention. In yet another aspect, the detectable species can be provided by dye-providing compositions that include an oxidizable compound capable of undergoing oxidative condensation with couplers such as those containing phenolic groups or activated methylene groups, together with such a coupler. Representative such oxidizable compounds include such compounds as benzidene and its homologs, p-phenylenediamines, p-aminophenols, 4-amino-antipyrine, etc. A wide range of such couplers, including a number of autocoupling compounds, is described in the literature, such as in Mees and James (supra) and in Kosar, *Light-Sensitive Systems*, 1965, pages 215–249.

Preferred dye-providing compositions include 4-methoxy-1-naphthol, an autocoupling species, and the combination of 4-aminoantipyrine (HCl) as an oxidizable compound together with 1,7-dihydroxynaphthalene as a coupler.

To facilitate the detection of any change produced in an element as described herein, such as change in coloration, optical density or fluorescence, the elements of this invention include a radiation-transmissive layer to receive any reaction products or other materials produced in a reagent layer, the relative presence or absence of which relates to detection of an analytical result. Such a layer, referred to herein as a registration layer, is free from indicating reagents, but is permeable to detectable species formed in the element and is in fluid contact with a reagent layer, at least under conditions of use. The registration layer may be separated from reagent layer(s) by a radiation-blocking layer, such as a reflecting and/or opaque layer, to facilitate result detection by various radiometric techniques. The registration layer, which is also desirably swellable in liquid under analysis, can include hydrophilic colloids such as those useful in reagent layers and is preferably non-fibrous. When a reagent layer is fibrous, non-fibrous radiation-blocking and registration layers in association therewith improve the apparent uniformity of an analytical result produced in such a reagent layer.

Where the detectable species produced in the element is a dye or other mordantable material, the registration layer may contain a mordant, such as those described as useful image dye mordants in color photographic films and papers. Exemplary mordants are materials such as vinylpyridine compounds of the quaternary ammonium groups such as those disclosed in U.S. Pat. Nos. 3,625,694; 3,758,445; 3,709,690; 3,488,706 and 3,557,006. A desirable mordant is N,N-dimethyl-N-benzyl-3-maleimidopropylammonium chloride.

As mentioned previously, elements of this invention can include a radiation-blocking layer, preferably interposed between a reagent layer and the registration layer. Radiation-blocking layers are permeable to the detectable species formed in the element and serve to inhibit passage of electromagnetic radiation, such as at the wavelength or wavelengths used for detection. Using such a layer, color or other potential interferants to result detection can be kept from the registration layer. Such layers include an opacifying agent that, by virtue of its absorbance, reflectance or the like, provides a radiation inhibiting effect when incorporated into the layer. In one aspect, the radiation-blocking layer can include a matrix containing an opacifying agent, such as a pigment like carbon or other inorganic pigment such as a metal salt like titanium dioxide, zinc oxide, barium sulfate, etc. Blushed polymers, which are generally reflective in nature, can comprise the opacifying agent and layers of such blushed polymers as are useful in spreading layers can be used also as radiation-blocking layers. It will be appreciated that if a microporous, blushed polymer layer is used as a radiation-blocking layer, such layer can also serve as a filtering layer. Such a layer is useful in the event that the registration layer is permeable to filterable substances which could impair result detection in the registration layer if allowed to enter the registration layer from the reagent layer.

In one preferred aspect, blushed polymer layers can also incorporate a reflective inorganic pigment, such as the highly reflective pigments mentioned elsewhere herein, to enhance spreading and/or reflectivity. The amount of pigment that can be included in a layer together with blushed polymer is highly variable, and amounts of from about 5 percent by weight to about 1,000 percent by weight of pigment based on the weight of blushed polymer are preferred, with a pigment concentration of from about 100 weight percent to about 600 weight percent pigment based on the blushed polymer being most preferred.

As mentioned previously, element of this invention can include an isotropically porous spreading layer. The spreading layer is a layer that can accept a liquid sample, whether applied directly to the spreading layer or provided to it from a layer or layers in fluid contact with the spreading layer, and within which the solvent or dispersion medium of the sample and at least one solute, dispersoid (constituent of the dispersed or internal phase) or reaction product of solute or dispersoid is distributed such that a uniform apparent concentration of such substance, i.e. solute, dispersoid or reaction product thereof (which can be an analyte or an analyte precursor), is provided at the surface of the spreading layer facing the reagent layer(s) of the element. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The mechanism of spreading is not fully understood, but it is believed that spreading results from and is limited by a combination of forces such as hydrostatic pressure of a liquid sample, capillary action within the spreading layer, surface tension of the sample, wicking action of layers in fluid contact with the spreading layer, and the like. As will be appreciated, the extent of spreading is dependent in part on the volume of liquid to be spread. However, it should be emphasized that the uniform apparent concentration obtained with spreading is substantially independent of liquid sample volume and will occur with varying degrees of spreading. As a result, elements of this invention do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g. one square centimeter), there is no need to remove excess moisture from the element after application of a liquid sample. Further, because spreading occurs in the spreading layer and the spread substance is provided to the fluid contacting reagent layer and without apparent substantial lateral hydrostatic pressure, there is not the "ringing" problem often seen with prior analytical elements.

The spreading layer need only produce a uniform apparent concentration of spread substance per unit area at its surface facing a reagent layer with which the spreading layer is in fluid contact, and it is very convenient to determine whether a particular layer can be suitable for spreading purposes. Such uniformity of apparent concentration can be determined by densitometric or other analytical techniques, as by scanning the appropriate surface or reagent layer or other associated layer to determine the apparent concentration of spread substance or of any reaction product based on the concentration of spread substance. The following test is intended only as an example and the selection of materials or test parameters does not indicate that other materials or parameters would not be suitable for similar purposes.

In conducting such a test one can apply to a transparent photographic film support material, such as subbed poly (ethylene terephthalate), a transparent gelatin layer at a gelatin coverage of about 200 mg/dm$^2$. The gelatin may vary in hardness, but for testing purposes a layer of gelatin hardened to swell the layer thickness by about 300% when immersed for 5 minutes in 22° C water is suitable. When dry, the gelatin layer will have a thickness of about 30 microns. Over the gelatin layer can be applied, such as by coating from solution or dispersion, the layer to be evaluated for spreading purposes. Spreading layers can be designed to have widely varying dry thicknesses, and a thickness of from about 100 to about 200 microns is convenient for test purposes. After drying the layers, a sample of test solution or dispersion can be applied to the surface of the spreading layer under evaluation, preferably in a small quantity so that not all portions of the layer are wetted by the applied sample, but desirably sufficient to create a wetted region such as one having a circular area of about 8–10 millimeters in diameter. The selection of a test solution or dispersion is a matter of choice and will depend in part on the type of sample or analyte to which the layer will be exposed under conditions of actual usage. For low molecular weight materials, aqueous dye solutions can be used and a .0005 weight percent solution of Solatine Pink$^R$ is acceptable. For higher molecular weight materials such as proteins, an aqueous dispersion of bovine albumin dyed with Solatine Pink$^R$ can be used. After applying the liquid sample to the layer under evaluation and allowing the liquid sample to disappear from the surface of and be taken up into the layer, the test element can be turned over and the bottom surface of the proposed spreading layer can be viewed through the transparent support material and gelatin layer. If, prior to substantial evaporation of solvent or dispersion medium, the test element exhibits a well-defined colored spot of a substantially uniform color density when scanned by a densitometer having an aperture of about 5 microns by 100 microns, then spreading and the achievement of a uniform apparent concentration at the bottom surface of the test layer and/or in the gelatin layer has taken place. By substantially uniform density is meant a density across the spot, with the exception of its periphery, having maximum and minimum values not more than about ±10% from the mean density. Due to edge effects, non-characteristic density gradients may arise at the spot periphery but need have no effect on the significance of an analytical result. Peripheral area can vary between spots, but it will usually not be more than about 20% of the entire spot and may be less.

As mentioned herein, useful spreading or metering layers are desirably isotropically porous layers. Such layers can be prepared using a variety of components. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers. Such microcrystalline materials are described in an article entitled, "Colloidal Macromolecular Phenomena, Part II, Novel Microcrystals of Polymers" by O.A. Battista et al published in the Journal of Applied Polymer Science, Vol. II, pages 481–498 (1967). Microcrystalline cellulose, which is commercially available from FMC Corporation under the name Avicel$^R$, is an example of such a colloidal material which is satisfactory for use in the present invention. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, non-adherent particles can be coated with a thin adherent layer, such as a solution of hydrophilic colloid like gelatin or polyvinyl alcohol, and brought into mutual contact in a layer. When the colloid coating dries, the layer integrity is maintained and open spaces remain between its component particles.

As an alternative or in addition to such particulate materials, the spreading layer can be prepared using isotropically porous polymer compositions. It is possible to prepare such polymer compositions using techniques useful in forming blushed polymers, for example, as described in U.S. Pat. No. 3,555,129. Other techniques useful in preparing isotropically porous polymer compositions include those relating to the use of gas or other swellable constituents to create pores, as described in U.S. Pat. Nos. 2,960,728 and 2,946,095; or to the use within the polymer phase of a dissolvable solid that is dissolved to provide pores, for example, as discussed in U.S. Pat. No. 3,816,575.

Blushed (or precipitated) polymer layers are particularly desirable and can be formed on a substrate by dissolving a polymer in a mixture of two liquids, one of which is a lower boiling, good solvent for the polymer and the other of which is of a higher boiling point and is a non-solvent or a poor solvent for the polymer. Such a polymer solution is then coated on the substrate, and dried under controlled condition. The lower boiling solvent evaporates more readily and the coating can become enriched in the liquid which is a poor solvent or non-solvent. As evaporation proceeds, under proper conditions, the polymer forms as an isotropically porous layer. Many different polymers can be used, singly or in combination, for preparing isotropically porous blushed polymer spreading layers for use in this invention, typical examples being polycarbonates, polyamides, polyurethanes and cellulose esters such as cellulose acetate. Various microporous filters are or are partly blushed polymeric compositions, for example, various membrane filters of Millipore Corporation, and they have been described in patents such as U.S. Pat. No. 2,783,894 and U.S. Pat. No. 2,772,322.

In preparing integral analytical elements of this invention, the layers can be preformed as separate layers which can thereafter be laminated prior to use or maintained as separate layers until brought into fluid contact when the element is in use. Layers preformed as separate members, if coatable, are typically coated from solution or dispersion on a surface from which the layer can be physically stripped when dried. However, a convenient procedure which can avoid problems of multiple stripping and lamination steps when contiguous layers are desired, is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well-known in the preparation of light-sensitive photographic films and papers. If it is essential or desirable that adjacent layers be discrete, and maintenance of layer separation by adjustment of coating formulation specifc gravity is not satisfactory, as possibly in the case of porous spreading layers, the appropriate selection of components for each layer, including solvent or dispersion medium, can minimize or eliminate interlayer component migration and solvent effects, thereby promoting the formation of well-defined, discrete layers. Any interlayer adhesion problems can be overcome without harmful effect by means of surface treatments including extremely thin application of subbing materials such as are used in photographic films.

For coatable reagent layers, a coating solution or dispersion including the matrix and incorporated interactive materials can be prepared, coated as discussed herein and dried to form a dimensionally stable layer. The thickness of any reagent layer and its degree of permeability are widely variable and depend on actual usage. Dry thickness of from about 10 microns to about 100 microns have been convenient, although more widely varying thicknesses may be preferable in certain circumstances. For example, if comparatively large amounts of interactive material, e.g., polymeric materials like enzymes, are required, it may be desirable to use slightly thicker reagent layers. Fibrous reagent layers can be formed by impregnation of a fibrous matrix, in accordance with well-known techniques.

Radiation-blocking layers and registration layers can be prepared using methods and thicknesses as used when preparing coatable reagent layers, but with constituents appropriate for the particular layer. In the case of registration layers, in addition to their permeability and radiation-transmissiveness, they are desirably substantially free from any characteristic that might appear as or contribute to mottle or other noise in the detection of an analytical result produced in an integral element of the invention. For example, any variations in color or in texture within the registration layer, as could occur if fibrous materials, e.g., some papers, are used as a permeable medium, may be disadvantageous due to non-uniform reflectance or transmittance of detecting energy. This is also true regarding layers, e.g., radiation-blocking and reagent layers, of which at least the lower surface would be observable by a detection means examining a radiation-transmissive registration layer. Further, although fibrous materials like filter and other papers are generally permeable overall, some such materials typically can exhibit widely ranging degrees of permeability and may not exhibit uniform permeability, for example, based on structural variations such as fiber dimensions and spacing. As a result, such materials are not preferred in registration layers and other layers of elements of the present invention intended for quantitative analytical work.

Spreading layers can also be prepared by coating from solution or dispersion. As stated previously, spreading and assocaited layers of an element are in a superposed relationship such that a spreading layer is in fluid contact with a reagent layer. The range of materials useful for inclusion in any spreading layer is widely variable as discussed herein and will usually include predominantly materials that are resistant to, i.e. substantially insoluble in and nonswellable upon contact with water or other liquid under analysis. Swelling of about 10–40% of the layer's dry thickness may be normal. The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers of from about 50 microns to about 300 microns have been particularly useful. However, wider variations in thickness are acceptable and may be desirable for particular elements.

When preparing an isotropically porous spreading layer, it is useful to have void volume comprise at least about 25% of the total layer volume, and void volumes of from 50–95% may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when isotropically porous blushed polymers are used in the spreading layer. The void volume of any such layer can be calculated with reasonable accuracy by a variety of techniques such as the statistical method described in Chalkley, *Journal of the National Cancer Institute*, 4, 47

(1943) and by direct weighing and determining the ratio of actual weight of the layer to the weight of solid material equal in volume to that of the layer, comparably composed of constituents from the layer. It will be appreciated that the pore size in any case should be sufficient to permit spreading of initial sample components or other substances desirably provided to a reagent layer.

As mentioned previously herein, the present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 200 nm and about 900 nm as well as radiation due to radioactivity. For fluorimetric detection of analytical results through the support, it is desirable for the support to transmit over a somewhat wider band that is necessary for non-fluorescence measurements, or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, the reagent layer, the radiation-blocking layer (if present) and the registration layer will usually be interposed in the element between the support and the spreading layer (if present), which often is the outermost layer in an element.

The components of any particular layer of an element of this invention, and the layer configuration of choice, will depend on the use for which an element is intended. As stated previously, spreading layer pore size can be chosen so that the layer can filter out undesirable sample components that would, for example, interfere with an analytical reaction or with the detection of any test result produced within the element. For analysis of whole blood, porous layers having a pore size of from 1 to about 5 microns are particularly useful in screening out blood cells, which typically have a size of from about 7 to about 30 microns. If desirable, an element can include a plurality of spreading layers, each of which may be different in its ability to spread and filter. Also, if a restraint on transport of substances within the element additional to that provided by spreading layers is needed, a filter or dialysis layer can be included at an appropriate location in the element. As an example, in analyzing the blood glucose, a dialysis layer such as a semipermeable cellulose membrane can prevent passage of proteins or other potentially interfering substances to the reagent layer.

In the layers of the element, it can be advantageous to incorporate one or more surfactant materials such as anionic and nonionic surfactant materials. They can, for example, enhance coatability of layer formulations and enhance the extent and rate of spreading in spreading layers that are not easily wetted by liquid samples in the absence of an acid such as a surfactant. Interactive materials can also be present in the spreading layer if desirable for a particular analysis. As an example, proteins or other higher molecular weight materials can, for convenience, be divided into more easily spreadable, lower molecular weight components that may also be more suitable for an analytical reaction, such as by having in the spreading layer an appropriate interactive material such as an enzyme, e.g., a protease or esterase. In layers of the element it can also be desirable to include materials that can render non-active in the analysis of choice by chemical reaction or otherwise, materials potentially deleterious to such analysis. As an example, ascorbate oxidase may be incorporated in an element to remove ascorbate ion which may interfere with analysis for glucose.

In still another aspect, an analysis of choice may require a multi-stage reaction that can best be accomplished in an element having a plurality of reagent layers, each of which may be adapted to enhance or effect particular reaction stages. As an example, in the determination of the enzyme known as serum glutamic-oxalacetic transaminase, sequential reactions can be used. This enzyme catalyzes the conversion at a pH of about 7.4 of $\alpha$-ketoglutarate and aspartate ions to the corresponding oxalacetate and glutamate. The oxalacetate can be measured via coupling with the diazonium salt of the dye known as "Fast Ponceau L". To facilitate the first equilibrium that should be established before coupling, it is desirable to separate the reagents and to incorporate each of them into a separate layer to provide a suitable time interval for the first equilibrium to be established without hindering the establishment of this first equilibrium by the premature starting of the second reaction. Thus the glutamic acid can be incorporated in a first reagent layer which is coated over a second reagent layer that contains the salt of the dye "Fast Ponceau L".

Analytical elements of the present invention can be adapted for use in carrying out a wide variety of chemical analyses, not only in the field of clinical chemistry but in chemical research and in chemical process control laboratories. They are well suited for use in clinical testing of body fluids, such as blood, blood serum and urine, since in this work a large number of repetitive tests are frequently conducted and test results are often needed a very short time after the sample is taken. In the field of blood analysis, for example, the multi-layer element can be adapted for use in carrying out quantitative analyses for many of the blood components which are routinely measured. Thus, for example, the element may be readily adapted for use in the analysis of such blood components as albumin, bilirubin, urea nitrogen, serum glutamic-oxalacetic transaminase, chloride, glucose, uric acid, and alkaline phosphatase, as well as many other components, by appropriate choice of test reagents or other interactive materials. In analyzing blood with the analytical element of this invention, the blood cells may first be separated from the serum, by such means as centrifuging, and the serum applied to the element. However, it is not necessary to make such separation, for example, if reflective spectrophotometric analysis techniques are used to quantify or otherwise analyze the reaction product formed in the element. Whole blood can be applied directly to the element and the blood cells filtered out and excluded from the registration layer through the action of a filtering layer, which can also be a radiation-blocking layer. The presence of these cells on the element will not interfere with spectrophotometric analysis if it is carried out by reflection techniques, with light being transmitted through the support and registration layer and reflected from the radiation-blocking layer or other reflecting layer such that detecting radiation does not intercept the cells. A particularly significant advantage of the integral analytical elements described herein is their ability to be used to analyze either serum or whole blood.

As can be appreciated, a variety of different elements, depending on the analysis of choice, can be prepared in accordance with the present invention. Elements can be configured in a variety of forms, including elongated tapes of any desired width, sheets or smaller chips. Particular elements can be adapted for one or more tests of a single type or a variety of tests of different types. In such latter event, it can be desirable to coat a common support with one or more strips or channels, each optionally of a different composition to form a composite element suited for conducting a variety of desired tests.

Figure 2:
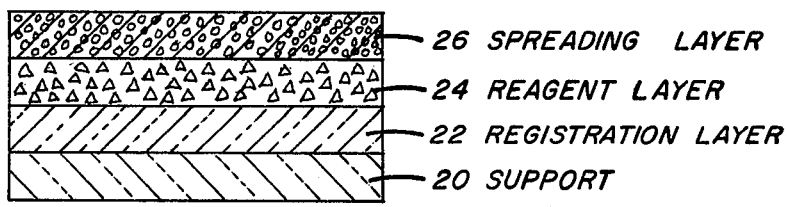
Figure 3:
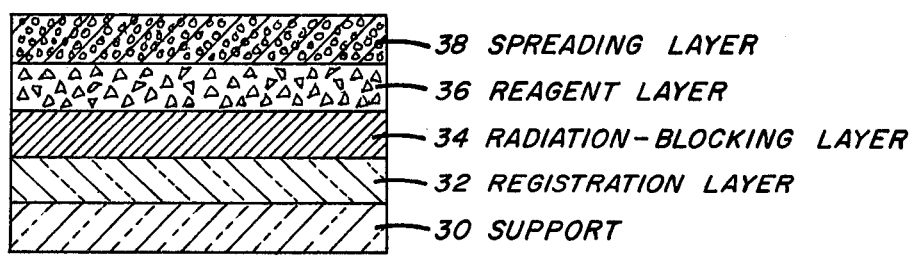

Exemplary elements of this invention include those illustrated in the accompanying drawings. In FIG. 1 is represented an analytical element composed of a radiation-transmissive support 10, on which is carried a registration layer 12, a radiation-blocking layer 14 which can filter as well as provide an appropriate background for analytical result detection such as by reflection spectrophotometry, and a reagent layer 16. Detection can be done through the support, which is suitably transmissive at the detecting wavelength. The registration layer 12 can be a hydrophilic colloid such as gelain. Reagent layer 16 can be composed of a solution or dispersion of one or more test reagents in a binder such as gelatin or in filter paper or other fibrous material, while layer 14 can be a blushed polymer having isotropic porosity and/or such pore size as may be needed for any filtering function it is intended to perform. The layers are shown in fluid contact. In an alternative embodiment of the invention shown in FIG. 2, the analytical element is composed of a radiation-transmissive support 20 bearing a registration layer 22 shown in fluid contact with a reagent layer 24 and a spreading layer 26 which can also serve the function of filtering and also may provide a suitably reflective background for reflection spectrophotometric detection through support 20. Alternatively, layer 26 may be such that it does not reflect and detection can be accomplished in the transmission mode. Layer 26 can be, for example, an isotropically porous blushed polymer layer which has been coated or laminated over layer 24. FIG. 3 illustrates a further embodiment of the invention in which the analytical element is composed of support 30, registration layer 32, a radiation-blocking layer 34 which can be formed from a dispersion of a pigment like titanium dioxide in a hydrophilic colloid such as gelatin, a reagent layer 36, and a spreading layer 38 such as an isotropically porous blushed polymer layer which can serve the functions of spreading and filtering. The various layers are in fluid contact.

Figure 4:
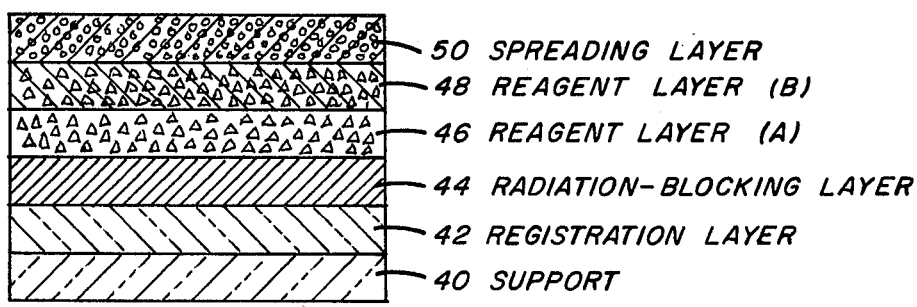
FIG. 4 is an enlarged sectional view of a preferred embodiment illustrating an integral analytical element of this invention.

A still further embodiment of the invention is shown in FIG. 4 in which the analytical element is composed of a support 40, a registration layer 42, a radiation-blocking/filtering layer 44, reagent layer (A) 46, a reagent layer (B) 48, and a spreading/filtering layer 50. Layer 44 can be composed, for example, of titanium dioxide in blushed cellulose acetate and layer 50 can be composed of diatomaceous earth in blushed cellulose acetate or of glass beads mutually adhered with a hydrophilic colloid like gelatin.

The present elements are placed in use by applying to the element a sample of liquid under analysis. Typically, an element will be formed such that an applied sample will contact a spreading layer, if present, prior to a non-spreading reagent layer and will first contact such spreading layer at its surface farther from such reagent layer. Because analytical accuracy of the present elements is not substantially diminished by variations in the volume of applied samples, especially when a spreading layer is present in the element, sample application by hand or machine is acceptable. For reasons of convenience in detecting an analytical result, however, reasonable consistency in sample volume may be desirable. As discussed previously, the spreading layer is also extremely desirable in minimizing the occurrence of ringing when soluble interactive materials are used in a reagent layer.

In a typical analytical procedure using the present elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, if present, the element is exposed to any conditioning, such as heating, humidification or the like, that may be desirable to quicken or otherwise facilitate obtaining any test result. If an automated procedure is used, it can also be desirable to have any spreading layer accomplish its function within several seconds, but allowing sufficient time to provide metering, which is contrasted with the almost instantaneous, unregulated diffusion as can be obtained with absorbent fibrous papers. This can be accomplished conveniently by appropriate selection of varous parameters, such as layer thickness, void volume in porous layers., etc.

After the analytical result is obtained as a detectable change, it is measured, usually by passing the element through a zone in which suitable apparatus for reflection, transmission of fluorescence spectrophotometry is provided. Such apparatus would serve to direct a beam of energy, such as light, through the support and the registration layer. The light would then be reflected, such as from a radiation-blocking layer in the element, back to a detecting means or would pass through the element to a detector, in the case of transmission detection. In a preferred mode, the analytical result is detected in a region of the element totally within the region in which such result is produced. Use of reflection spectrophotometry can be advantageous in some situations as it can effectively avoid interference fron residues, such as blood cells, which may have been left on or in the layers of the element. Conventional techniques of fluorescence spectrophotometry can also be employed if the detectable species is a fluorescent material. Detection would be acccomplished using energy that excites the fluorescent species and a detector that senses its fluorescent emission. Furthermore, when blood serum is tested or means are provided for eliminating unwanted whole blood residues, transmission techniques can be used to detect and quantify the indicating reaction products by directing a flow of radiant energy, for example, U.V. visible or I.R. radiation at one surface of the element and measuring the output of that energy from the opposing surface of the element. Generally, electromagnetic radiation in the range of from about 200 to about 900 nm has been found useful for such measurements although any radiation to which the element is permeable and which is capable of quantifying the product produced in the reagent layer can be used.

Various calibration techniques can be used to provide a control for the analysis. As one example, a sample of analyte standard solution can be applied adjacent to the area where the drop of sample is placed in order to permit the use of differential measurements in the analysis.

The following example of integral analytical elements are provided to further illustrate the present invention.

EXAMPLE 1

On a thick (180 microns) support of poly(ethylene terephthalate), having a gelatin sub, are successively applied:
1. a registration (receiving) layer containing, per square meter, 2.5 g. of gelatin, 2.15 g of a mordant (copolymer of styrene and N,N-dimethyl-N-3-maleimidopropylammonium chloride);
2. a porous, reflective radiation-blocking layer containing, per square meter, 151 g of gelatin and 11.4 g of titanium dioxide;
3. a reagent (analytical) layer containing, per square meter, 17.5 g of gelatin, 1.5 g of 1-naphthal-2-sulfonic acid potassium salt, 0.73 g of disodium phosphate buffer, 0.45 g of monopotassium phosphate buffer, 0.38 g of 4-aminoantipyrine (HCl) 1.6 g of glycerine as a plasticizer, 0.09 g of peroxyidase (14014 U/m$^2$) and 0.374 g of glucose oxidase (40440 U/m$^2$);
4. a spreading layer containing, per square meter, 97 g of cellulose acetate and 65.5 g of titanium dioxide.

The thusly prepared element is used for the analysis of glucose solutions, the concentrations of which are varied from 0 to 800 mg per deciliter. On samples of the element are deposited drops, each of which represents 10 μl of an aqueous glucose solution. After 1 hour, the density of the colorations is measured by reflection using a Macbeth Densitometer (Model TD-504).

When the glucose solution is applied to the surface of the element, it spreads within layer (4) and is metered to layer (3) wherein the glucose reacts with the oxygen and the water in the presence of the glucose oxidase to provide gluconic acid and hydrogen peroxide; these compounds, in the presence of peroxidase, react with the 4-aminoantipyrine which is then oxidized; the oxidation product of the 4-aminoantipyrine then reacts by coupling with the 1-naphthol-2-sulfonic acid potassium salt to form a dye which diffuses out of the reagent layer (3), through the radiation-blocking layer (2) and into the registration layer (1) where it is detected using the Macbeth TD-504 densitometer. The results are summarized in the table following Example 2.

EXAMPLE 2

An analytical element, having a structure identical to that of Example 1 is prepared, except that the registration layer (1) contains gelatin as the only component, at a coating weight of 4.30 g per square meter. The product is used according to the procedures described in Example 1, and the results obtained are summarized in the table hereunder.

TABLE

| Element | Glucose content of sample (mg/deciliter) | Density measured by white-light reflection |
|---|---|---|
| Example 1 | 0 | 0.28 |
|  | 100 | 0.36 |
|  | 150 | 0.37 |
|  | 200 | 0.40 |
|  | 300 | 0.47 |
|  | 400 | 0.52 |
|  | 600 | 0.53 |
|  | 800 | 0.53 |
| Example 2 | 0 | 0.23 |
|  | 100 | 0.36 |
|  | 150 | 0.42 |
|  | 200 | 0.47 |
|  | 300 | 0.54 |
|  | 400 | 0.55 |
|  | 600 | 0.56 |
|  | 800 | 0.60 |

The invention has been described in detail with particular reference to certain preferred embodiments thereof, but it will be understood that variations and modifications can be effected within the spirit and scope of the invention.

There is claimed:

1. An integral element for analysis of liquids, the element comprising,
    a reagent layer comprising a composition that is interactive in the presence of a predetermined analyte to provide a diffusible, detectable species,
    a non-fibrous radiation-blocking layer, permeable to the detectable species and comprising an opacifying agent,
    a radiation-transmissive registration layer, permeable to the detectable species, within which said species can be detected and comprising a non-fibrous material,
    wherein the radiation-blocking layer is interposed between the registration layer and the reagent layer.

2. An integral element for analysis of liquids, the element comprising a radiation-transmissive support having thereon,
    a reagent layer comprising a composition that is interactive in the presence of a predetermined analyte to provide a diffusible, detectable species,
    a non-fibrous radiation-blocking layer, permeable to the detectable species and comprising an opacifying agent, and
    a radiation-transmissive registration layer, permeable to the detectable species, within which said species can be detected and comprising a non-fibrous material,
    wherein the registration layer is interposed between the support and the radiation-blocking layer and the radiation-blocking layer is interposed between the registration layer and the reagent layer.

3. An integral element as described in claim 2 wherein the reagent layer and the registration layer are water-swellable and wherein the opacifying agent in the radiation-blocking layer comprises a pigment.

4. An integral element as described in claim 3 wherein the reagent layer comprises a hydrophilic colloid having the interactive material distributed therein, the radiation-blocking layer comprises a hydrophilic colloid having a pigment distributed therein and the registration layer comprises a hydrophilic colloid.

5. An integral element as described in claim 4 wherein the registration layer further comprises a mordant for the detectable species.

6. An integral element for analysis of liquids, the element comprising, an isotropically porous spreading layer comprising a non-fibrous material, a reagent layer comprising a composition that is interactive in the presence of a predetermined analyte to provide a diffusible, detectable species, and a radiation-transmissive registration layer, permeable to the detectable species, within which said species can be detected and comprising a non-fibrous material wherein the reagent layer is interposed between the registration layer and the spreading layer.

7. An integral element for analysis of liquids, the element comprising a radiation-transmissive support having thereon, an isotropically porous spreading layer comprising a non-fibrous material, a reagent layer comprising a composition comprising material interactive in the presence of a predetermined analyte to provide a diffusible, detectable species, and a radiation-transmissive registration layer, permeable to the detectable species, within which said species can be detected and comprising a non-fibrous material, wherein the registration layer is interposed between the support and the reagent layer and the reagent layer is interposed between the registration layer and the spreading layer.

8. An integral element as described in claim 7, further comprising a non-fibrous radiation-blocking layer, permeable to the detectable species, comprising an opacifying agent and interposed between the registration layer and the reagent layer.

9. An integral element for analysis of liquids the element comprising a radiation-transmissive support having thereon, a water-resistant, isotropically porous spreading layer comprising a non-fibrous material, a water-swellable reagent layer comprising a composition that is interactive in the presence of a predetermined analyte to provide a diffusible, detectable species, a non-fibrous, radiation-blocking layer, permeable to the detectable species and comprising an opacifying agent, and a radiation-transmissive registration layer, permeable to the detectable species, within which said species can be detected and comprising a water-swellable, non-fibrous material, wherein the registration layer is the closest to the support of said layers the radiation-blocking layer is interposed between the reagent layer and the registration layer, and the reagent layer is interposed between the radiation-blocking layer and the spreading layer.

10. An integral element for analysis of liquids, the element comprising a radiation-transmissive support having thereon, a water-resistant, isotropically porous spreading layer comprising a non-fibrous polymeric composition or particulate matter, a water-swellable reagent layer comprising a composition that is interactive in the presence of a predetermined analyte to provide a diffusible detectable species, a non-fibrous radiation-blocking layer, permeable to the detectable species and comprising an opacifying agent, and a water-swellable, non-fibrous radiation-transmissive registration layer, permeable to the detectable species and within which said species can be detected, wherein the registration layer is the closest to the support of said layers, the radiation-blocking layer is interposed between the reagent layer and the registration layer, and the reagent layer is interposed between the radiation-blocking layer and the spreading layer.

11. An integral element as described in claim 10 wherein the spreading layer comprises a blushed polymer.

12. An integral element as described in claim 10 wherein the spreading layer comprises particulate matter comprising a pigment, a colloid derived from a polymer, glass beads or resinous beads.

13. An integral element as described in claim 10 wherein the opacifying agent in the radiation-blocking layer comprises a water-resistant, blushed polymer.

14. An integral element as described in claim 9 wherein the opacifying agent in the radiation-blocking layer comprises a pigment.

15. An integral element for analysis of liquids, the element comprisng a radiation-transmissive support having thereon, a water-resistant, isotropically porous spreading layer comprising a blushed polymer and a surfactant, a reagent layer comprising a water-swellable hydrophilic colloid having distributed therein a composition that is interactive in the presence of a predetermined analyte to provide a diffusible, detectable species, a radiation-blocking layer permeable to the detectable species and comprising a hydrophilic colloid having a pigment distributed therein, and a water-swellable, radiation-transmissive registration layer, permeable to the detectable species, within which said species can be detected and comprising a hydrophilic colloid, wherein the registration layer is the closest to the support of said layers the radiation-blocking layer is interposed between the reagent layer and the registration layer, and the reagent layer is interposed between the radiation-blocking layer and the spreading layer.

16. An integral element as described in claim 15 wherein the registration layer further comprises a mordant for the detectable species.

17. An integral element as described in claim 15 wherein the spreading layer additionally comprises an inorganic pigment.

18. An integral element for analysis of liquids, the element comprising a radition-transmissive support having thereon, a water-resistant, isotropically porous spreading layer comprising a blushed polymer selected from cellulose acetate and a polyamide, an inorganic pigment and a surfactant, a water-swellable reagent layer comprising a hydrophilic colloid selected from gelatin, poly(vinyl alcohol), poly(vinyl pyrrolidone), an acrylamide, agarose and a polysaccharide, said colloid having distributed therein a composition that is interactive in the presence of a predetermined analyte to provide a diffusible detectable species, a radiation-blocking layer, permeable to the detectable species and comprising a hydrophilic colloid selected from gelatin, poly(vinyl alcohol), poly(vinyl pyrrolidone), an acrylamide, agarose and a polysaccharide, said colloid having distributed therein a pigment selected from carbon, titanium dioxide and barium sulfate and a water-swellable, radiation-transmissive registration layer, permeable to the detectable species, within which said species can be detected and comprising a hydrophilic colloid selected from gelatin, poly(vinyl alcohol), poly(vinyl pyrrolidone), an acrylamide, agarose and a polysaccharide, and a mordant for the detectable species, wherein the registration layer is the closest to the support of said layers, the radiation-blocking layer is interposed between the reagent layer and the registration layer, and the reagent layer is interposed between the radiation-blocking layer and the spreading layer.

19. An integral element as described in claim 18 wherein the composition in the reagent layer comprises glucose oxidase, peroxidase and an indicator composition comprising a compound oxidizable in the presence of hydrogen peroxide and peroxidase to effect formation of a dye.

20. An integral element as described in claim 19 wherein the indicator composition comprises aminoantipyrene chlorohydrate and 1-naphthol-2-sulfonic acid sodium salt and the mordant in the registration layer comprises a copolymer comprising recurring units of styrene and N,N-dimethyl-N-benzyl-3-maleimidopropylammonium chloride.

* * * * *

UNITED STATES PATENT AND TRADEMARK OFFICE
CERTIFICATE OF CORRECTION

PATENT NO. : 4,042,335
DATED : August 16, 1977
INVENTOR(S) : Pierre L. Clément

It is certified that error appears in the above-identified patent and that said Letters Patent are hereby corrected as shown below:

Title page, item [56], under "U.S. PATENT DOCUMENTS", line 4, "TD" should read --TP--.

Title page, item [56], under "U.S. PATENT DOCUMENTS", line 6, "X" should read --XR--.

Column 3, line 15, "3,672,432" should read --2,672,432--.

Column 3, line 62, "response in" should read --response is--.

Column 6, line 12, "electromagetic" should read --electromagnetic--.

Column 6, line 48, "Flinned" should read --Flinn ed--.

Column 6, lines 58-59, "unifomly" should read --uniformly--.

Column 7, line 39, "flu id" should read --fluid--.

Column 9, line 5, "be" should be deleted.

Column 9, line 25, "non-fibrious" should read --non-fibrous--.

Column 9, line 26, "isotropicaly" should read --isotropically--.

Column 9, line 26, "on" should read --in--.

Column 9, line 42, "unfirmly" should read --uniformly--.

Column 15, line 64, "thickness" should read --thicknesses--.

UNITED STATES PATENT AND TRADEMARK OFFICE
CERTIFICATE OF CORRECTION

PATENT NO. : 4,042,335
DATED : August 16, 1977            Page 2 of 2
INVENTOR(S) : Pierre L. Clément It is certified that error appears in the above-identified patent and that said Letters Patent are hereby corrected as shown below:

Column 16, line 34, "assocaited" should read --associated--.

Column 17, line 66, "acid" should read --aid--.

Column 20, line 33, "varous" should read --various--.

Column 20, line 38, "of" should read --or--.

Column 20, line 49, "fron" should read "from".

Column 20, line 54, "acccomplished" should read --accomplished--.

Column 21, line 15, "2.5" should read --2.15--.

Column 23, line 35, after "liquids", --,-- should be inserted.

Column 24, line 23, "comprisng" should read --comprising--.

Signed and Sealed this

Seventh Day of February 1978

[SEAL]

Attest:

RUTH C. MASON
Attesting Officer

LUTRELLE F. PARKER
Acting Commissioner of Patents and Trademarks